(12) United States Patent
Klyachko et al.

(10) Patent No.: US 8,071,339 B2
(45) Date of Patent: Dec. 6, 2011

(54) MUTANT PHOSPHORIBOSYLPYROPHOSPHATE SYNTHETASE AND METHOD FOR PRODUCING L-HISTIDINE

(75) Inventors: Elena Vitalievna Klyachko, Moscow (RU); Rustem Saidovich Shakulov, Moscow (RU); Yuri Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 965 days.

(21) Appl. No.: 12/031,757

(22) Filed: Feb. 15, 2008

(65) Prior Publication Data

US 2009/0275089 A1  Nov. 5, 2009

Related U.S. Application Data

(62) Division of application No. 10/984,821, filed on Nov. 10, 2004, now abandoned.

(60) Provisional application No. 60/587,492, filed on Jul. 14, 2004.

(30) Foreign Application Priority Data

Nov. 10, 2003  (RU) .............................. 2003132412
Jul. 7, 2004  (RU) .............................. 2004120501

(51) Int. Cl.
*C12P 13/24* (2006.01)
*C12P 13/04* (2006.01)
*C12P 21/06* (2006.01)
*C12N 9/10* (2006.01)
*C12N 9/12* (2006.01)
*C12N 1/20* (2006.01)
*C12N 15/74* (2006.01)
*C12N 15/00* (2006.01)

(52) U.S. Cl. ........ 435/107; 435/106; 435/193; 435/194; 435/252.3; 435/252.33; 435/252.8; 435/471; 435/488; 435/69.1; 435/320.1

(58) Field of Classification Search .................. 435/107, 435/106, 193, 194, 252.3, 252.33, 252.8, 435/471, 488, 69.1, 320.1
See application file for complete search history.

(56) References Cited

U.S. PATENT DOCUMENTS

| | | | |
|---|---|---|---|
| 4,278,765 A | | 7/1981 | Debabov et al. |
| 4,927,758 A | * | 5/1990 | Mizukami et al. ............ 435/107 |
| 5,661,012 A | | 8/1997 | Sano et al. |
| 6,040,160 A | | 3/2000 | Kojima et al. |
| 6,258,554 B1 | * | 7/2001 | Ikeda et al. ..................... 435/41 |
| 6,297,031 B1 | | 10/2001 | Debabov et al. |
| 6,653,111 B2 | | 11/2003 | Debabov et al. |
| 6,960,455 B2 | | 11/2005 | Livshits et al. |
| 7,138,266 B2 | | 11/2006 | Debabov et al. |
| 7,179,623 B2 | | 2/2007 | Livshits et al. |
| 7,186,531 B2 | | 3/2007 | Akhverdian et al. |
| 7,259,003 B2 | | 8/2007 | Livshits et al. |
| 7,300,786 B2 | | 11/2007 | Klyachko et al. |
| 2002/0061569 A1 | | 5/2002 | Haselbeck et al. |
| 2004/0132165 A1 | | 7/2004 | Akhverdian et al. |
| 2004/0229320 A1 | | 11/2004 | Stoynova et al. |
| 2004/0229321 A1 | | 11/2004 | Savrasova et al. |
| 2005/0048631 A1 | | 3/2005 | Klyachko et al. |
| 2005/0106688 A1 | | 5/2005 | Imaizumi et al. |
| 2005/0214911 A1 | | 9/2005 | Marchenko et al. |
| 2006/0035346 A1 | | 2/2006 | Savrasova et al. |
| 2006/0040365 A1 | | 2/2006 | Kozlov et al. |
| 2006/0088919 A1 | | 4/2006 | Rybak et al. |
| 2006/0141586 A1 | | 6/2006 | Rybak et al. |
| 2006/0160192 A1 | | 7/2006 | Rybak et al. |
| 2006/0286643 A1 | | 12/2006 | Sheremet'eva et al. |
| 2007/0184532 A1 | | 8/2007 | Klyachko et al. |
| 2007/0212764 A1 | | 9/2007 | Ptitsyn et al. |

FOREIGN PATENT DOCUMENTS

EP  1 004 663  5/2000
JP  56-018596  2/1981

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Wishart et al., A single mutation converts a novel phosphotyrosine binding domain into a dual-specificity phosphatase. J. Biol. Chem., 1995, vol. 270(45): 26782-26785.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*

(Continued)

*Primary Examiner* — Ganapathirama Raghu
(74) *Attorney, Agent, or Firm* — Shelly Guest Cermak; Cermak Nakajima LLP

(57) ABSTRACT

The present invention relates to a mutant bacterial PRPP synthetase which is resistant to feedback by purine nucleotides, and a method for producing L-histidine using the bacterium of the Enterobacteriaceae family wherein the L-amino acid productivity of said bacterium is enhanced by use of the PRPP synthetase which is resistant to feedback by purine nucleotides, coded by the mutant prsA gene.

7 Claims, No Drawings

OTHER PUBLICATIONS

Becker, M. A., et al., "The Genetic and Functional Basis of Purine Nucleotide Feedback-resistant Phosphoribosylpyrophosphate Synthetase Superactivity", J. Clin. Invest. 1995;96:2133-2141.

Hove-Jensen, B., et al., "Phosphoribosylpyrophosphate Synthetase of *Escherichia coli*," J. Biol. Chem. 1986;261(15):6765-6771.

Krath, B. N., et al., "Implications of secondary structure comparison of class I and class II phosphoribosyl diphosphate synthetase on catalysis, regulation, and quaternary structure," Protein Sci. 2001;10(11):2317-2324.

Roessler, B. J., et al., "Human X-linked Phosphoribosylpyrophosphate Synthetase Superactivity Is Associated With Distinct Point Mutations in the PRPS1 Gene," J. Biol Chem. 1993;268(35):26476-26481.

Tachibana, M., et al., "Mammalian phosphoribosyl-pyrophosphate synthetase," Avd. Enz. Reg. 1995;35:229-249.

Taira, M., et al., "Nucleotide and Deduced Amino Acid Sequences of Two Distinct cDNAs for Rat Phosphoribosylpyrophosphate Synthetase," J. Biol. Chem. 1987;262(31):14867-14870.

Zoref, E., et al., "Mutant Feedback-Resistant Phosphoribosylpyrophosphate Synthetase Associated with Purine Overproduction and Gout," J. Clin. Invest. 1975;56:1093-1099.

Search Report for EP Patent App. No. 04026719.7 (Jan. 13, 2005).

Hove-Jensen, B., "Mutation in the Phosphoribosylpyrophosphate Synthetase Gene (*prs*) That Results in Simultaneous Requirements for Purine and Pyrimidine Nucleosides, Nicotinamide Nucleotide, Histidine, and Tryptophan in *Escherichia coli*," J. Bacteriol. 1988;170(3):1148-1152.

Notice of Reason for Rejection for Japanese Patent App. No. 2004-326981 (Jun. 11, 2010) with English translation thereof.

U.S. Appl. No. 60/586,222, filed Jul. 9, 2004, Akhverdian et al.
U.S. Appl. No. 60/587,492, filed Jul. 14, 2004, Klyachko et al.
U.S. Appl. No. 60/610,545, filed Sep. 17, 2004, Marchenko et al.
U.S. Appl. No. 60/644,562, filed Jan. 19, 2005, Rybak et al.
U.S. Appl. No. 60/673,807, filed Apr. 22, 2005, Rybak et al.
U.S. Appl. No. 60/693,507, filed Jun. 24, 2005, Rybak et al.
U.S. Appl. No. 60/693,509, filed Jun. 24, 2005, Sheremet'eva et al.
U.S. Appl. No. 60/703,414, filed Jul. 29, 2005, Ptitsyn et al.
U.S. Appl. No. 60/703,426, filed Jul. 29, 2005, Rybak et al.
U.S. Appl. No. 60/714,843, filed Sep. 8, 2005, Filippov et al.
U.S. Appl. No. 60/714,850, filed Sep. 8, 2005, Gulevich et al.
U.S. Appl. No. 60/723,566, filed Oct. 5, 2005, Rybak et al.
U.S. Appl. No. 60/723,924, filed Oct. 6, 2005, Rybak et al.
U.S. Appl. No. 60/723,925, filed Oct. 6, 2005, Rybak et al.
U.S. Appl. No. 60/743,222, filed Feb. 3, 2006, Rybak et al.
U.S. Appl. No. 60/743,257, filed Feb. 8, 2006, Rybak et al.
U.S. Appl. No. 60/743,258, filed Feb. 9, 2006, Rybak et al.
U.S. Appl. No. 60/806,819, filed Jul. 10, 2006, Rybak et al.
U.S. Appl. No. 60/826,820, filed Sep. 25, 2006, Kotliarova et al.
U.S. Appl. No. 11/536,863, filed Sep. 29, 2006, Zakataeva et al.
U.S. Appl. No. 60/867,151, filed Nov. 24, 2006, Rybak et al.
U.S. Appl. No. 60/885,671, filed Jan. 19, 2007, Altman et al.
U.S. Appl. No. 60/894,996, filed Mar. 15, 2007, Rybak et al.
U.S. Appl. No. 11/830,961, filed Jul. 31, 2007, Filippov et al.
U.S. Appl. No. 11/830,969, filed Jul. 31, 2007, Gulevich et al.
U.S. Appl. No. 11/830,974, filed Sep. 4, 2007, Filippov et al.
U.S. Appl. No. 11/849,403, filed Sep. 4, 2007, Rybak et al.
U.S. Appl. No. 11/952,297, filed Dec. 7, 2007, Rybak et al.
U.S. Appl. No. 12/022,299, filed Jan. 30, 2008, Rybak et al.

* cited by examiner

SEQUENCE LISTING

<160> NUMBER OF SEQ ID NOS: 7

<210> SEQ ID NO 1
<211> LENGTH: 948
<212> TYPE: DNA
<213> ORGANISM: Escherichia coli
<220> FEATURE:
<221> NAME/KEY: CDS
<222> LOCATION: (1)..(948)

<400> SEQUENCE: 1

```
gtg cct gat atg aag ctt ttt gct ggt aac gcc acc ccg gaa cta gca    48
Val Pro Asp Met Lys Leu Phe Ala Gly Asn Ala Thr Pro Glu Leu Ala
 1               5                  10                  15 caa cgt att gcc aac cgc ctg tac act tca ctc ggc gac gcc gct gta    96
Gln Arg Ile Ala Asn Arg Leu Tyr Thr Ser Leu Gly Asp Ala Ala Val
             20                  25                  30 ggt cgc ttt agc gat ggc gaa gtc agc gta caa att aat gaa aat gta   144
Gly Arg Phe Ser Asp Gly Glu Val Ser Val Gln Ile Asn Glu Asn Val
         35                  40                  45 cgc ggt ggt gat att ttc atc atc cag tcc act tgt gcc cct act aac   192
Arg Gly Gly Asp Ile Phe Ile Ile Gln Ser Thr Cys Ala Pro Thr Asn
     50                  55                  60 gac aac ctg atg gaa tta gtc gtt atg gtt gat gcc ctg cgt cgt gct   240
Asp Asn Leu Met Glu Leu Val Val Met Val Asp Ala Leu Arg Arg Ala
 65                  70                  75                  80 tcc gca ggt cgt atc acc gct gtt atc ccc tac ttt ggc tat gcg cgc   288
Ser Ala Gly Arg Ile Thr Ala Val Ile Pro Tyr Phe Gly Tyr Ala Arg
                 85                  90                  95 cag gac cgt cgc gtc cgt tcc gct cgt gta cca atc act gcg aaa gtg   336
Gln Asp Arg Arg Val Arg Ser Ala Arg Val Pro Ile Thr Ala Lys Val
            100                 105                 110 gtt gca gac ttc ctc tcc agc gtc ggt gtt gac cgt gtg ctg aca gtg   384
Val Ala Asp Phe Leu Ser Ser Val Gly Val Asp Arg Val Leu Thr Val
        115                 120                 125 gat ctg cac gct gaa cag att cag ggt ttc ttc gac gtt ccg gtt gat   432
Asp Leu His Ala Glu Gln Ile Gln Gly Phe Phe Asp Val Pro Val Asp
    130                 135                 140 aac gta ttt ggt agc ccg atc ctg ctg gaa gac atg ctg cag ctg aat   480
Asn Val Phe Gly Ser Pro Ile Leu Leu Glu Asp Met Leu Gln Leu Asn
145                 150                 155                 160 ctg gat aac cca att gtg gtt tct ccg gac atc ggc ggc gtt gtg cgt   528
Leu Asp Asn Pro Ile Val Val Ser Pro Asp Ile Gly Gly Val Val Arg
                165                 170                 175 gcc cgc gct atc gct aag ctg ctg aac gat acc gat atg gca atc atc   576
Ala Arg Ala Ile Ala Lys Leu Leu Asn Asp Thr Asp Met Ala Ile Ile
            180                 185                 190
```

```
gac aaa cgt cgt ccg cgt gcg aac gtt tca cag gtg atg cat atc atc      624
Asp Lys Arg Arg Pro Arg Ala Asn Val Ser Gln Val Met His Ile Ile
        195                 200                 205 ggt gac gtt gca ggt cgt gac tgc gta ctg gtc gat gat atg atc gac      672
Gly Asp Val Ala Gly Arg Asp Cys Val Leu Val Asp Asp Met Ile Asp
210                 215                 220 act ggc ggt acg ctg tgt aaa gct gct gaa gct ctg aaa gaa cgt ggt      720
Thr Gly Gly Thr Leu Cys Lys Ala Ala Glu Ala Leu Lys Glu Arg Gly
225                 230                 235                 240 gct aaa cgt gta ttt gcg tac gcg act cac ccg atc ttc tct ggc aac      768
Ala Lys Arg Val Phe Ala Tyr Ala Thr His Pro Ile Phe Ser Gly Asn
        245                 250                 255 gcg gcg aac aac ctg cgt aac tct gta att gat gaa gtc gtt gtc tgc      816
Ala Ala Asn Asn Leu Arg Asn Ser Val Ile Asp Glu Val Val Val Cys
        260                 265                 270 gat acc att ccg ctg agc gat gaa atc aaa tca ctg ccg aac gtg cgt      864
Asp Thr Ile Pro Leu Ser Asp Glu Ile Lys Ser Leu Pro Asn Val Arg
        275                 280                 285 act ctg acc ctg tca ggt atg ctg gcc gaa gcg att cgt cgt atc agc      912
Thr Leu Thr Leu Ser Gly Met Leu Ala Glu Ala Ile Arg Arg Ile Ser
290                 295                 300 aac gaa gaa tcg atc tct gcc atg ttc gaa cac taa                      948
Asn Glu Glu Ser Ile Ser Ala Met Phe Glu His
305                 310                 315

<210> SEQ ID NO 2
<211> LENGTH: 315
<212> TYPE: PRT
<213> ORGANISM: Escherichia coli

<400> SEQUENCE: 2

Val Pro Asp Met Lys Leu Phe Ala Gly Asn Ala Thr Pro Glu Leu Ala
1               5                   10                  15

Gln Arg Ile Ala Asn Arg Leu Tyr Thr Ser Leu Gly Asp Ala Ala Val
            20                  25                  30

Gly Arg Phe Ser Asp Gly Glu Val Ser Val Gln Ile Asn Glu Asn Val
        35                  40                  45

Arg Gly Gly Asp Ile Phe Ile Ile Gln Ser Thr Cys Ala Pro Thr Asn
50                  55                  60

Asp Asn Leu Met Glu Leu Val Val Met Val Asp Ala Leu Arg Arg Ala
65                  70                  75                  80

Ser Ala Gly Arg Ile Thr Ala Val Ile Pro Tyr Phe Gly Tyr Ala Arg
                85                  90                  95

Gln Asp Arg Arg Val Arg Ser Ala Arg Val Pro Ile Thr Ala Lys Val
            100                 105                 110

Val Ala Asp Phe Leu Ser Ser Val Gly Val Asp Arg Val Leu Thr Val
        115                 120                 125

Asp Leu His Ala Glu Gln Ile Gln Gly Phe Phe Asp Val Pro Val Asp
130                 135                 140

Asn Val Phe Gly Ser Pro Ile Leu Leu Glu Asp Met Leu Gln Leu Asn
145                 150                 155                 160

Leu Asp Asn Pro Ile Val Val Ser Pro Asp Ile Gly Gly Val Val Arg
                165                 170                 175

Ala Arg Ala Ile Ala Lys Leu Leu Asn Asp Thr Asp Met Ala Ile Ile
            180                 185                 190

Asp Lys Arg Arg Pro Arg Ala Asn Val Ser Gln Val Met His Ile Ile
        195                 200                 205
```

-continued

```
Gly Asp Val Ala Gly Arg Asp Cys Val Leu Val Asp Met Ile Asp
    210                 215                 220

Thr Gly Gly Thr Leu Cys Lys Ala Ala Glu Ala Leu Lys Glu Arg Gly
225                 230                 235                 240

Ala Lys Arg Val Phe Ala Tyr Ala Thr His Pro Ile Phe Ser Gly Asn
                245                 250                 255

Ala Ala Asn Asn Leu Arg Asn Ser Val Ile Asp Glu Val Val Cys
            260                 265                 270

Asp Thr Ile Pro Leu Ser Asp Glu Ile Lys Ser Leu Pro Asn Val Arg
        275                 280                 285

Thr Leu Thr Leu Ser Gly Met Leu Ala Glu Ala Ile Arg Arg Ile Ser
    290                 295                 300

Asn Glu Glu Ser Ile Ser Ala Met Phe Glu His
305                 310                 315
```

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 3
ctctctagag ccgggttcga ttagtgttc                                    29

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 4
ctcagatctt gcctaaggat cttctcatgc ctgatatg                          38

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 5
aaagtggttg caagcttcct ctc                                          23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 6
gagaggaagc ttgcaaccac ttt                                          23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 7
cgcgcttcaa atgaaacaga t                                            21

MUTANT PHOSPHORIBOSYLPYROPHOSPHATE SYNTHETASE AND METHOD FOR PRODUCING L-HISTIDINE

This application is a divisional patent application under 35 U.S.C. §120 of U.S. patent application Ser. No. 10/984,821, filed Nov. 10, 2004, now abandoned, which claims priority under 35 U.S.C. §119(a) to Russian Patent Application Number 2003132412, filed Nov. 10, 2003, Russian Patent Application Number 2004120501, filed Jul. 7, 2004, and U.S. Provisional Patent Application No. 60/587,492, filed Jul. 14, 2004, the entireties of which are incorporated by reference. The Sequence Listing filed electronically herewith is also hereby incorporated by reference in its entirety (File Name: US-117D_Seq_List_Copy__1; File Size: 9 KB; Date Created: Feb. 15, 2008).

BACKGROUND OF THE INVENTION

1. Technical Field

The present invention relates to a method for producing L-amino acid, such as L-histidine. More specifically, the present invention relates to a novel feedback-resistant enzyme involved in the biosynthesis of purines and L-histidine. More specifically, the present invention concerns a new feedback-resistant mutant phosphoribosylpyrophosphate synthetase (PRPP synthetase) from *E. coli*. The invention also relates to a method for producing L-histidine by fermentation using bacterial strains containing the novel feedback-resistant enzyme.

2. Background Art

Conventionally, L-amino acids are industrially produced by fermentation methods utilizing strains of microorganisms obtained from natural sources or mutants thereof, which are modified to enhance production yields of L-amino acids.

Many techniques to enhance production yields of L-amino acids have been reported, including transformation of microorganisms with recombinant DNA (see, for example, U.S. Pat. No. 4,278,765). Other techniques include increasing the activities of enzymes involved in amino acid biosynthesis and/or desensitizing the target enzymes of the feedback inhibition by the resulting L-amino acid (see, for example, Japanese Laid-open application No. 56-18596 (1981), WO 95/16042 or U.S. Pat. Nos. 5,661,012 and 6,040,160).

5-Phosphoribosyl-α-1-pyrophosphate (hereinafter, "PRPP") and adenosine-5'-triphosphate (hereinafter, "ATP") are the initial substrates in histidine biosynthesis. PRPP can sometimes induce the histidine biosynthesis to follow divergent pathways, resulting in the biosynthesis of pyrimidine nucleotides, purine nucleotides, pyridine nucleotides, and tryptophan (*Escherichia coli* and *Salmonella*, Second Edition, Editor in Chief: F. C. Neidhardt, ASM Press, Washington D.C., 1996).

Many nucleotides competitively inhibit the activity of PRPP synthetase with ATP. However, the only potent nucleotide inhibitor is adenosine-5'-diphosphate (ADP); it competes with ATP and is an allosteric inhibitor that binds to a site other than the active site (Hove-Jensen, B. et al, J. Biol. Chem. 261:6765-6771 (1986)).

Mutants with altered PRPP synthetase have been obtained in both *E. coli* and *S. typhimurium*. One of the *E. coli* mutants produces a PRPP synthetase with a 27-fold increase in the $K_m$ value for ATP, and the enzyme is no longer inhibited by AMP. This mutation results from substitution of aspartic acid 128 by alanine (prsDA mutation). One *S. typhimurium* prs mutant is temperature-sensitive and has only 20% of the wild-type PRPP synthetase activity. This mutant enzyme had elevated $K_m$ values for ATP and ribose 5-phosphate and reduced sensitivity to inhibition by ADP. The mutation is the result of the replacement of arginine 78 by cysteine (*Escherichia coli* and *Salmonella*, Second Edition, Editor in Chief: F. C. Neidhardt, ASM Press, Washington D.C., 1996).

It is well known that superactivity of human PRPP synthetase and resistance to purine nucleotide are associated with neurodevelopmental abnormalities in addition to hyperuricemia and gout (Becker M. A. et al, Arthritis Rheum, 18:6 Suppl: 687-94 (1975); Zoref E. et al, J. Clin. Invest., 56(5): 1093-9 (1975)). Uric acid overproduction in individuals with superactivity of PRPP synthetase results from increased production of PRPP and consequent acceleration of purine nucleotide synthesis de novo. It was shown that superactivity of PRPP synthetase is a result of an A to G mutation at nucleotide 341, which results in an asparagine to serine substitution at amino acid residue 113 of the mature enzyme. This mutant PRPP synthetase is resistant to purine nucleotides that inhibit the normal enzyme by a mechanism that is noncompetitive with respect to ATP (Roessler, B. J. et al. J. Biol. Chem., v. 268, No 35, 26476-26481 (1993); Becker, M. A. et al, J. Clin. Invest., 96(5): 2133-41 (1995)).

A process for producing purine nucleosides via fermentation of a microorganism belonging to the genus *Escherichia* and having purine nucleoside-producing ability, and containing a prsDA mutation is disclosed (European patent application EP1004663A1). However, there are no reports describing mutant bacterial PRPP synthetase which is feedback-resistant to purine nucleotides, or the use of such a mutant PRPP synthetase for improving L-histidine production using L-histidine-producing strains.

SUMMARY OF THE INVENTION

An object of the present invention is to provide a new mutant bacterial PRPP synthetase. Furthermore, it is an object of the present invention to provide an L-histidine-producing strain containing the mutant PRPP synthetase, which has enhanced production yields of L-histidine. Also, it is an object of the present invention to provide a method for producing L-histidine using the above-described strain.

It is an object of the present invention to provide a mutant bacterial phosphoribosylpyrophosphate synthetase (PRPP synthetase), wherein the aspartic acid at position 115 in a wild-type phosphoribosylpyrophosphate synthetase from *Escherichia coli* is substituted with another L-amino acid residue, and feedback inhibition by purine nucleotides is desensitized.

It is a further object of the present invention to provide the mutant PRPP synthetase described above, wherein the aspartic acid residue at position 115 in a wild-type PRPP synthetase is substituted with an serine residue.

It is a further object of the present invention to provide the mutant PRPP synthetase as described above, wherein the wild-type PRPP synthetase is derived from *Escherichia coli*.

It is a further object of the present invention to provide the mutant PRPP synthetase as described above, which includes deletion, substitution, insertion, or addition of one or several amino acids at one or a plurality of positions other than position 115, wherein feedback inhibition by purine nucleotides is desensitized.

It is a further object of the present invention to provide a DNA encoding a mutant PRPP synthetase as described above.

It is a further object of the present invention to provide a bacterium of the Enterobacteriaceae family, which contains the DNA described above, and has an ability to produce L-histidine.

It is a further object of the present invention to provide the bacterium as described above, wherein the activity of the mutant PRPP synthetase is enhanced.

It is a further object of the present invention to provide the bacterium as described above, wherein the bacterium belongs to the genus *Escherichia*.

It is a further object of the present invention to provide the bacterium as described above, wherein the activity of the mutant PRPP synthetase is enhanced by increasing the expression of the mutant PRPP synthetase gene.

It is a further object of the present invention to provide the bacterium as described above, wherein the activity of the mutant PRPP synthetase is enhanced by increasing the copy number of the mutant PRPP synthetase gene, or modifying an expression control sequence of the gene so that the expression of the gene is enhanced.

It is a further object of the present invention to provide the bacterium as described above, wherein the copy number is increased by integration of additional copies of the mutant PRPP synthetase gene into the chromosome of the bacterium.

It is a further object of the present invention to provide a method for producing L-histidine comprising cultivating the bacterium as described above in a culture medium, allowing the L-histidine to accumulate in the culture medium, and collecting the L-histidine from the culture medium.

It is a further object of the present invention to provide the method as described above, wherein the bacterium has enhanced expression of the genes for histidine biosynthesis.

DESCRIPTION OF THE PREFERRED EMBODIMENTS

The above-described objects were achieved by constructing a new mutant PRPP synthetase from *E. coli*. Based on the high conservatism of the prsA gene (Taira M. et al., J. Biol. Chem., v. 262, No 31, pp. 14867-14870 (1987)), the mutant *E. coli* PRPP synthetase having a mutation corresponding to the human mutation Asn-113 was constructed. It was shown that the use of such a mutant PRPP synthetase enhances L-histidine production when additional copies of the gene encoding the mutant PRPP synthetase are introduced into a L-histidine-producing strain. Thus, the present invention has been completed.

Mutant PRPP Synthetase and Mutant prsA Gene.

The mutant PRPP synthetase of the present invention is referred to as "the mutant PRPP synthetase" hereinafter and is defined as having a substitution at the aspartic acid residue at position 115 of wild-type PRPP synthetase. A DNA coding for the mutant PRPP synthetase is referred to as "the mutant prsA gene" or "mutant PRPP synthetase gene," and a PRPP synthetase without the above position 115 substitution is referred to as "wild-type PRPP synthetase."

It is known that the genetic and functional basis of super-activity of human PRPP synthetase associated with resistance to purine nucleotide is caused by single base substitution in prsA gene (Roessler, B. J. et al. J. Biol. Chem., v. 268, No 35, 26476-26481 (1993)). Based on the high conservatism of prsA gene (Taira M. et al., J. Biol. Chem., v. 262, No 31, pp. 14867-14870 (1987)), the mutant PRPP synthetase from *E. coli* having a mutation corresponding to the human Asn-113 mutation was constructed. This mutation has never been described for all bacterial PRPP synthetases. The phrase "bacterial PRPP synthetase" means the PRPP synthetase existing in the bacteria of Enterobacteriaceae family, coryne-bacteria, bacteria belonging to the genus *Bacillus* etc. Enterobacteriaceae family includes bacteria belonging to the genera *Escherichia*, *Erwinia*, *Providencia* and *Serratia*. The genus *Escherichia* is preferred.

The substitution of the aspartic acid at position 115 of wild-type PRPP synthetase [EC 2.7.6.1] from *E. coli* with any amino acid, preferably with serine, leads to formation of a mutant protein which is feedback-resistant to purine nucleotides, such as purine di- and mononucleotides, mainly guanosine-5'-diphosphate (GDP), adenosine-5'-diphosphate (ADP) and adenosine-5'-monophosphate (AMP).

The mutant PRPP synthetase can be obtained by introducing mutations into a wild-type prsA gene using known methods. The prsA gene of *E. coli* (nucleotide numbers 1260151 to 1261098 in the sequence of GenBank Accession NC_000913, gi:16129170, SEQ ID NO: 1) is one example of a wild-type prsA gene. The prsA gene is located between the ychM and ychB ORFs on the chromosome of *E. coli* strain K-12. Therefore, the prsA gene can be obtained by PCR (polymerase chain reaction; see White, T. J. et al., Trends Genet., 5, 185 (1989)) utilizing primers prepared based on the nucleotide sequence of the gene. Genes coding for PRPP synthetase of other microorganisms can be obtained in a similar manner.

The mutant PRPP synthetase may include deletion, substitution, insertion, or addition of one or several amino acids at one or a plurality of positions other than 115, provided that the activity of PRPP synthetase is not lost. The phrase "activity of PRPP synthetase" means an activity catalyzing the reaction of ribose-5-phosphate and ATP with release of AMP to form 5-phosphoribosyl-α-1-pyrophosphate (PRPP). The PRPP synthetase activity of the extracts and degrees of inhibition by ADP can be measured using the partially modified method of K. F. Jensen et al. (Analytical Biochemistry, 98, 254-263 (1979)). Specifically, $[\alpha\text{-}^{32}P]$ATP can be used as the substrate and $[^{32}P]$AMP produced by the reaction should be measured.

The number of "several" amino acids differs depending on the position or type of amino acid in the three dimensional structure of the protein. This is because some amino acids have high homology to one another and therefore do not greatly affect the three dimensional structure of the protein. Therefore, the mutant PRPP synthetase of the present invention may be one which has homology of not less than 30 to 50%, preferably 50 to 70%, more preferably 70% to 90%, and most preferably 95% or more, with respect to the entire PRPP synthetase amino acid sequence, and which retains the PRPP synthetase activity.

In the present invention, "position 115" means position 115 in the amino acid sequence of SEQ ID NO: 2. In the PRPP synthetase from *E. coli*, the amino acid residue in position 115 is aspartic acid. A position of an amino acid residue may change, for example, if an amino acid residue is inserted at the N-terminus portion, the amino acid residue inherently located at position 115 becomes position 116. In this situation, the amino acid residue corresponding to the original position 115 is to mean the amino acid residue at position 115 in the present invention.

To determine the L-amino acid residue corresponding to position 115 of PRPP synthetase from *E. coli*, it is necessary to align the amino acid sequence of PRPP synthetase from *E. coli* (SEQ ID NO: 2) and an amino acid sequence of PRPP synthetase from the bacterium of interest.

The DNA of the present invention, which codes for the substantially the same protein as the mutant PRPP synthetase described above, may be obtained, for example, by modifying the nucleotide sequence, for example, by means of site-directed mutagenesis so that one or more amino acid residues at a specified site are deleted, substituted, inserted, or added. The DNA modified as described above may be obtained by conventionally known mutation treatments. Mutation treatments include a method for treating in vitro a DNA containing the mutant prsA gene, for example, with hydroxylamine, and a method for treating a microorganism, for example, a bacterium, belonging to the genus *Escherichia* containing the mutant prsA gene with ultraviolet irradiation or a mutating agent usually used for the such treatment, such as N-methyl-N'-nitro-N-nitrosoguanidine (NTG) and nitrous acid.

The substitution, deletion, insertion, or addition of a nucleotide as described above also includes mutation, which naturally occurs (mutant or variant), for example, on the basis of the individual difference or the difference in species or genus of bacterium, which contains PRPP synthetase.

The DNA, which codes for substantially the same protein as the mutant PRPP synthetase, can be obtained by isolating a DNA which hybridizes as a probe to DNA having a known prsA gene sequence or part of it, under stringent conditions, and which codes for a protein having the PRPP synthetase activity. The DNA may be isolated from a cell containing the mutant PRPP synthetase which is subjected to mutation treatment.

The phrase "stringent conditions" in the present invention means conditions under which so-called specific hybrids are formed, and non-specific hybrids are not formed. It is difficult to express this condition precisely by a numerical value. However, for example, stringent conditions include conditions under which DNAs having high homology, for example, DNAs having homology of not less than 50% with each other hybridize to each other, and DNAs having homology lower than the above will not hybridize with each other.

To evaluate the degree of protein or DNA homology, several calculation methods, such as BLAST search, FASTA search and CrustalW, can be used.

BLAST (Basic Local Alignment Search Tool) is the heuristic search algorithm employed by the programs blastp, blastn, blastx, megablast, tblastn, and tblastx; these programs ascribe significance to their findings using the statistical methods of Karlin, Samuel and Stephen F. Altschul ("Methods for assessing the statistical significance of molecular sequence features by using general scoring schemes". Proc. Natl. Acad. Sci. USA, 1990, 87:2264-68; "Applications and statistics for multiple high-scoring segments in molecular sequences". Proc. Natl. Acad. Sci. USA, 1993, 90:5873-7). FASTA search method described by W. R. Pearson ("Rapid and Sensitive Sequence Comparison with FASTP and FASTA", Methods in Enzymology, 1990 183:63-98). ClustalW method described by Thompson J. D., Higgins D. G. and Gibson T. J. ("CLUSTAL W: improving the sensitivity of progressive multiple sequence alignment through sequence weighting, position-specific gap penalties and weight matrix choice", Nucleic Acids Res. 1994, 22:4673-4680).

Alternatively, stringent conditions are exemplified by conditions under which DNAs hybridize with each other at a salt concentration corresponding to ordinary conditions of washing in Southern hybridization, i.e., 60° C., 1×SSC, 0.1% SDS, preferably 0.1×SSC, 0.1% SDS. As a probe for the DNA that codes for variants and hybridizes with prsA gene, a partial sequence of the nucleotide sequence of SEQ ID NO: 1 can also be used. Such a probe may be prepared by PCR using oligonucleotides based on the nucleotide sequence of SEQ ID NO: 1 as primers, and a DNA fragment containing the nucleotide sequence of SEQ ID NO: 1 as a template. When a DNA fragment of about 300 bp is used as the probe, the washing conditions for the hybridization consist of, for example, 50° C., 2×SSC, and 0.1% SDS. Duration of the washing procedure depends on the type of membrane used for blotting and, as a rule, is recommended by manufacturer. For example, recommended duration of washing the Hybond™ N+ nylon membrane (Amersham) under stringent conditions is 15 minutes.

The gene, which is hybridizable under conditions as described above, includes those having a stop codon generated within a coding region of the gene, and those having no activity due to mutation of the active center. However, such inconveniences can be easily removed by ligating the gene with a commercially available expression vector, and investigating the PRPP synthetase activity of the expressed protein.

(2) Bacterium of the Present Invention.

The bacterium of the present invention is an L-histidine-producing bacterium of the Enterobacteriaceae family containing DNA encoding the mutant PRPP synthetase of the present invention. Furthermore, the bacterium of the present invention is an L-histidine-producing bacterium of the Enterobacteriaceae family having increased activity of mutant PRPP synthetase of the present invention. More specifically, the bacterium of the present invention is an L-histidine-producing bacterium of Enterobacteriaceae family, wherein L-histidine production by the bacterium is enhanced by enhancing an activity of the protein of the present invention in the bacterium. More preferably, the bacterium of the present invention is an L-histidine-producing bacterium belonging to the genus *Escherichia*, wherein L-histidine production by the bacterium is enhanced by enhancing an activity of the protein of the present invention, namely mutant PRPP synthetase, in the bacterium. More preferably, the bacterium of present invention contains the DNA encoding the mutant prsA gene, which is overexpressed by the chromosome or by a plasmid in the bacterium. As a result, the bacterium of the present invention has enhanced ability to produce L-histidine.

"Bacterium, which has an ability to produce L-histidine" means a bacterium which has an ability to cause accumulation of L-histidine in a medium, when the bacterium of the present invention is cultured in the medium. The L-histidine-producing ability may be imparted or enhanced by breeding. The term "bacterium, which has an ability to produce L-histidine" used herein also means a bacterium, which is able to produce and cause accumulation of L-histidine in a culture medium in an amount larger than a wild-type or parental strain, and preferably means that the bacterium is able to produce and cause accumulation of L-histidine in a medium in an amount of not less than 0.5 g/L, more preferably not less than 1.0 g/L.

Enterobacteriaceae family includes bacteria belonging to the genera *Escherichia*, *Erwinia*, *Providencia* and *Serratia*. The genus *Escherichia* is preferred.

The term "a bacterium belonging to the genus *Escherichia*" means the bacterium which is classified as the genus *Escherichia* according to the classification known to a person skilled in the art of microbiology. Examples of microorganisms belonging to the genus *Escherichia* used in the present invention include, but are not limited to *Escherichia coli* (*E. coli*).

The phrase "activity of the mutant PRPP synthetase is enhanced" means that the activity per cell is higher as compared to a non-modified strain, for example, a wild-type strain. For example, this meaning includes increasing the number of mutant PRPP synthetase molecules per cell, increasing the specific activity per mutant PRPP synthetase molecule, and so forth. Furthermore, *Escherichia coli* K-12 is an example of a wild-type strain that may serve as control. As a result of enhancement of intracellular activity of the mutant PRPP synthetase, an increase in the amount of L-histidine accumulation in a medium is observed.

Enhancement of the mutant PRPP synthetase activity in a bacterial cell can be attained by enhancement of expression of a gene coding for the mutant PRPP synthetase. The mutant PRPP synthetase gene of the present invention may encompass any of the genes encoding mutant PRPP synthetase derived from bacteria of Enterobacteriaceae family as well as the genes derived from other bacteria such as coryneform bacteria. Among these, genes derived from bacteria belonging to the genus *Escherichia* are preferred.

Transformation of a bacterium with a DNA encoding a protein means introduction of the DNA into a bacterium cell using conventional methods. As a result, expression of the gene encoding the protein of present invention is increased and the activity of the protein is enhanced in the bacterial cell.

Methods of enhancement of gene expression include increasing the gene copy number. Introduction of a gene into a vector that is able to function in a bacterium belonging to the genus *Escherichia* will increase the copy number of the gene. For such purposes, multi-copy vectors are preferably used. The multi-copy vector is exemplified by pBR322, pUC19, pBluescript KS+, pACYC177, pACYC184, pAYC32, pMW119, pET22b or the like. Other methods of gene expression enhancement can be achieved by introduction of multiple copies of the gene into the bacterial chromosome by, for example, methods of homologous recombination, or the like.

Other methods of gene expression enhancement can be achieved by placing the DNA of the present invention under the control of a more potent promoter instead of the native promoter. The strength of a promoter is defined by the frequency of RNA synthesis initiation. Methods for evaluating the strength of a promoter and examples of potent promoters are described by Deuschle, U., Kammerer, W., Gentz, R., Bujard, H. (Promoters in *Escherichia coli*: a hierarchy of in vivo strength indicates alternate structures. EMBO J. 1986, 5, 2987-2994). For example, the $P_R$ promoter is known as a potent constitutive promoter. Other known potent promoters are $P_L$ promoter, lac promoter, trp promoter, trc promoter, of lambda phage and the like.

The enhancement of translation can be achieved by introducing a more efficient Shine-Dalgarno sequence (SD sequence) into the DNA of the present invention in place of the native SD sequence. The SD sequence is typically a region upstream of the start codon of the mRNA interacting with the 16S RNA of ribosome (Shine J. and Dalgarno L., Proc. Natl. Acad. Sci. U S A, 1974, 71, 4, 1342-6).

Use of a more potent promoter can be combined with multiplication of gene copies.

Preparation of Chromosomal DNA, Hybridization, PCR, Plasmid DNA Preparation, DNA digestion and ligation, transformation, selection of an oligonucleotide as a primer, and the like, are all methods well known to one skilled in the art. These methods are described in Sambrook, J., and Russell D., "Molecular Cloning A Laboratory Manual, Third Edition", Cold Spring Harbor Laboratory Press (2001), and the like.

The bacterium of the present invention can be obtained by introduction of the aforementioned DNAs into a bacterium inherently having the ability to produce L-histidine. Alternatively, the bacterium of present invention can be obtained by imparting an ability to produce L-histidine to a bacterium already containing the DNAs.

The parent strain to be enhanced in activity of the protein of the present invention includes but is not limited to a bacteria belonging to the genus *Escherichia* having L-histidine producing ability, the L-histidine producing bacterium strains belonging to the genus *Escherichia*, such as *E. coli* strain 24 (VKPM B-5945, Russian patent 2003677); *E. coli* strain 80 (VKPM B-7270, Russian patent 2119536); *E. coli* strains NRRL B-12116-B12121 (U.S. Pat. No. 4,388,405); *E. coli* strains H-9342 (FERM BP-6675) and H-9343 (FERM BP-6676) (U.S. Pat. No. 6,344,347); *E. coli* strain H-9341 (FERM BP-6674) (European patent application 1085087A2); *E. coli* strain AI80/pFM201 (U.S. Pat. No. 6,258,554), and the like.

It is preferable that the L-histidine-producing bacterium be further modified to have enhanced expression of L-histidine biosynthesis. Genes effective for L-histidine biosynthesis include hisG gene and genes of hisBHAFI operon, preferably hisG gene encoding ATP phosphoribosyl transferase wherein feedback inhibition by L-histidine is desensitized (Russian patents 2003677 and 2119536).

(3) Method of the Present Invention.

The method of present invention includes a method for producing L-histidine, including the steps of cultivating the bacterium of the present invention in a culture medium, allowing the L-histidine to accumulate in the culture medium, and collecting the L-histidine from the culture medium.

In the present invention, the cultivation, collection, and purification of L-histidine from the medium and the like may be performed by conventional fermentation methods for producing amino acids using a microorganism. The medium used for culture may be either synthetic or natural, so long as the medium includes a carbon source, a nitrogen source, minerals and, if necessary, appropriate amounts of nutrients which the microorganism requires for growth. The carbon source may include various carbohydrates such as glucose and sucrose, and various organic acids. Depending on the mode of assimilation used by the chosen microorganism, alcohol including ethanol and glycerol may be used. The nitrogen source may include various ammonium salts, such as ammonia and ammonium sulfate, other nitrogen compounds, such as amines, a natural nitrogen source, such as peptone, soybean-hydrolysate, and digested fermentative microorganisms. Minerals may include potassium monophosphate, magnesium sulfate, sodium chloride, ferrous sulfate, manganese sulfate, calcium chloride, and the like. Some additional nutrients may be added to the medium, if necessary. For instance, if the microorganism requires proline for growth (proline auxotrophy), a sufficient amount of proline may be added to the cultivation medium.

The cultivation is performed preferably under aerobic conditions such as a shaking culture, and stirring culture with aeration, at a temperature of 20 to 42° C., preferably 37 to 40° C. The pH of the culture is usually between 5 and 9, preferably between 6.5 and 7.2. The pH of the culture can be adjusted with ammonia, calcium carbonate, various acids, various bases, and buffers. Usually, a 1- to 5-day cultivation leads to accumulation of the target L-amino acid in the liquid medium.

After cultivation, solids such as cells can be removed from the liquid medium by centrifugation or membrane filtration, and then the target L-amino acid can be collected and purified by ion-exchange, concentration and crystallization methods.

EXAMPLES

The present invention will be more concretely explained below with reference to the following non-limiting examples. In the examples, an amino acid is of L-configuration unless otherwise noted.

Example 1

Cloning of the Wild-Type prsA Gene from *E. coli* and Construction of the Mutant prsDA and prsDS Genes The entire nucleotide sequence of *E. coli* strain K-12 has been reported (Science, 277, 1453-1474, 1997). Based on the reported nucleotide sequence, the primers depicted in SEQ ID No. 3 (primer 1) and SEQ ID No.4 (primer 2) were synthesized and used for amplification of prsA gene. The primer 1 contains a BglII recognition site introduced at the 5' thereof. The primer 2 contains a XbaI recognition site introduced at the 5'-end thereof.

Chromosomal DNA of *E. coli* K12 was used as template for PCR, and was prepared by an ordinary method. PCR was carried out on the Applied Biosystems GeneAmp PCR System 2400 under the following conditions: initial DNA denaturation at 95° C. for 3 min; followed by 30 cycles of denaturation at 95° C. for 30 sec, annealing at 60° C. for 60 sec and elongation at 72° C. for 120 sec; and the final polymerization for 7 min at 72° C. using Taq polymerase (Fermentas, Lithuania). The resulting PCR fragment containing prsA gene without a promoter was treated with BglII and XbaI and inserted under $P_R$ promoter into the integrative vector pMW119-$P_R$ previously treated with the same enzymes. Vector pMW119-$P_R$ was constructed from a commercially available vector pMW119 by insertion of $P_R$ promoter from phageλ and attR and attL sites necessary for further Mu-integration. Thus, plasmid pMW-$P_R$-prsA was obtained.

Mutant prsDA gene (substitution of aspartic acid 128 with alanine in the PRPP synthetase coded by mutant prsDA gene) was obtained by PCR as described above using primers 1 (SEQ ID No. 3) and 2 (SEQ ID No. 4), and using plasmid pUCprsDA as a template. Plasmid pUCprsDA is described in detail in the European patent application EP1004663A1. The resulting PCR product was treated with BglII and XbaI and inserted under the control of the $P_R$ promoter into the integrative vector pMW119-$P_R$ previously treated with the same enzymes. Thus, plasmid pMW-$P_R$-prsDA was obtained.

Mutant prsDS gene (substitution of aspartic acid 115 with serine in the PRPP synthetase coded by mutant prsDS gene) was constructed by two successive PCR runs. First, two fragments of the gene were synthesized using primers 1 (SEQ ID No. 3) and 3 (SEQ ID No. 5) for the first fragment, and primers 2 (SEQ ID No. 4) and 4 (SEQ ID No. 6) for the second one. Chromosomal DNA of *E. coli* K12 was used as a template. Then the resulting PCR products were separated by electrophoresis and eluted from gel. In the second PCR run, these two DNA fragments were annealed and the mutant prsDS gene was completed. The resulting PCR fragment containing prsDS gene without a promoter was treated with BglII and XbaI and inserted under the control of the $P_R$ promoter into the integrative vector pMW119-$P_R$ previously treated with the same enzymes. Thus, plasmid pMW-$P_R$-prsDS was obtained.

Example 2

Effect of Enhanced Expression of the purH Gene on Histidine Production

Three L-histidine-producing plasmid-less strains containing additional copies of the prsA, prsDA or prsDS genes integrated into the bacterial chromosome were constructed. The L-histidine producing *E. coli* strain 80 was used as a parental strain for integration of the prsA, prsDA and prsDS genes into the bacterial chromosome. The strain 80 is described in Russian patent 2119536 and deposited in the Russian National Collection of Industrial Microorganisms (Russia, 113545 Moscow, 1$^{st}$ Dorozhny proezd, 1) under accession number VRPM B-7270.

Integration of the genes into the chromosome of strain 80 was performed in two steps. For the first step, the histidine-producing strain 80 was transformed with a helper plasmid containing replicon rep(p15A), transposase gene (genes cts62, ner, A, B from phage Mu-cts) and containing Tet$^R$ marker. For the second step, the resulting strain was transformed with plasmid pMW-$P_R$-prsA, pMW-$P_R$-prsDA or pMW-$P_R$-prsDS. For integration of the gene into the chromosome the heat-shocked cells were transferred to 1 ml of L-broth, incubated at 44° C. for 20 minutes, then at 37° C. for 40 minutes, and then were spread onto L-agar containing 10 µg/ml of tetracycline and 100 µg/ml of ampicillin. Colonies grown within 48 hours at 30° C. were inoculated in 1 ml of L broth and incubated for 72 hours at 42° C. in tubes. About 10 colonies from every tube were checked for ampicillin and tetracycline resistance. Colonies sensitive to both antibiotics were tested for presence of additional copies of the prs gene in the chromosome by PCR using primers 1 (SEQ ID No 3) and primer 5 (SEQ ID No 7). Primer 5 contains a sequence complementary to the attR site of phage Mu. For that purpose, a freshly isolated colony was suspended in 50 µl of water and then 1 µl was subject to PCR. PCR conditions were the following: initial DNA denaturation at 95° C. for 5 minutes; then 30 cycles of denaturation at 95° C. for 30 sec, annealing at 57° C. for 60 sec and elongation at 72° C. for 120 sec; the final polymerization at 72° C. for 7 min. A few of the antibiotic-sensitive colonies tested contained the necessary 1515 bp DNA fragment. Thus, strains 80::$P_R$-prsA, 80::$P_R$-prsDA, and 80::$P_R$-prsDS were obtained.

For mini-jar batch-fermentation one loop of each strain grown on L-agar was transferred to L-broth and cultivated at 30° C. with rotation (140 rpm) to reach an optical density of culture $OD_{540} \approx 2.0$. Then 25 ml of seed culture was added to 250 ml of medium for fermentation and cultivated at 29° C. for with rotation (1500 rpm). Duration of the batch-fermentation was approximately 35-40 hours. After the cultivation, the amount of histidine which accumulated in the medium was determined by paper chromatography. The paper was developed with a mobile phase: n-butanol: acetic acid:water=4:1:1 (v/v). A solution of ninhydrin (0.5%) in acetone was used as a visualizing reagent.

The composition of the fermentation medium (pH 6.0) (g/l):

| | |
|---|---|
| Glucose | 100.0 |
| Mameno | 0.2 of TN |
| $(NH_4)_2SO_4$ | 8.0 |
| $KH_2PO_4$ | 1.0 |
| $MgSO_4 \times 7H_2O$ | 0.4 |
| $FeSO_4 \times 7H_2O$ | 0.02 |
| $MnSO_4$ | 0.02 |
| Thiamine | 0.001 |
| Betaine | 2.0 |
| L-proline | 0.8 |
| L-glutamate | 3.0 |
| L-aspartate | 1.0 |
| Adenosine | 0.1 |

Obtained data are presented in the Table 1:

As it seen from the Table 1, the use of mutant prsDS gene coding for PRPP synthetase feedback resistant to purine nucleotides improved histidine productivity of the *E. coli* strain 80.

While the invention has been described with reference to preferred embodiments thereof, it will be apparent to one skilled in the art that various changes can be made, and equivalents employed, without departing from the scope of the invention. Each of the aforementioned documents is incorporated by reference herein in its entirety.

TABLE 1

| Strain | Integrated gene | DCW, g/l | Histidine, g/l | Yield per glucose (%) |
|---|---|---|---|---|
| 80 | — | 8.4 | 16.9 | 20.40 |
| 80::$P_R$-prsA | prsA | 8.6 | 15.6 | 19.1 |
| 80::$P_R$-prsDA | prsDA | 7.3 | 15.8 | 19.7 |
| 80::$P_R$-prsDS | prsDS | 8.5 | 18.4 | 22.1 |

We claim:

1. A method for producing L-histidine comprising cultivating a bacterium of the Enterobacteriaceae family in a culture medium, allowing said L-histidine to accumulate in the culture medium, and collecting said L-histidine from the culture medium, wherein said bacterium contains a DNA encoding a mutant phosphoribosylpyrophosphate synthetase (PRPP synthetase) comprising
   a) an amino acid sequence of a wild-type bacterial phosphoribosylpyrophosphate synthetase comprising the sequence of SEQ ID NO: 2, except that the aspartic acid at position 115 is substituted with another L-amino acid, or
   b) the mutant phosphoribosylpyrophosphate synthetase as described in (a), wherein one or more amino acids other than the aspartic acid at position 115 are deleted, substituted, inserted, or added, wherein said amino acid sequence is at least 95% homologous with respect to the entire amino acid sequence of SEQ ID NO: 2,
   wherein said phosphoribosylpyrophosphate synthetase activity is maintained, and feedback inhibition by purine nucleotides is desensitized.

2. The method of claim 1, said aspartic acid at position 115 is replaced by a serine residue.

3. The method of claim 1, wherein said bacterium belongs to genus *Escherichia*.

4. The method of claim 1, wherein said bacterium is *Escherichia coli*.

5. The method of claim 1, wherein said bacterium is transformed with said DNA.

6. The method of claim 1, wherein said bacterium of the Enterobacteriaceae family has enhanced expression of the genes for histidine biosynthesis, wherein said enhanced expression is obtained by a method selected from the group consisting of:
   A) increasing the copy number of said genes,
   B) replacing the native promoter of said genes with a more potent promoter,
   C) replacing the native Shine-Dalgarno sequence of said genes with a more efficient Shine-Dalgarno sequence, and
   D) combinations thereof.

7. The method of claim 6, wherein said genes for histidine biosynthesis are selected from the group consisting of hisG gene, hisBHAFI operon, and combinations thereof.

* * * * *